(12) United States Patent
Mathew et al.

(10) Patent No.: US 7,041,499 B2
(45) Date of Patent: May 9, 2006

(54) IMMUNO ACTIVATION OF CS1 RECEPTOR IN NATURAL KILLER CELLS TO INHIBIT TUMOR CELL GROWTH

(75) Inventors: Porunellor A. Mathew, Coppell, TX (US); Kent Boles, Fort Worth, TX (US)

(73) Assignee: University of North Texas Health Science Center, Fort Worth, TX (US)

( * ) Notice: Subject to any disclaimer, the term of this patent is extended or adjusted under 35 U.S.C. 154(b) by 53 days.

(21) Appl. No.: 10/021,741

(22) Filed: Dec. 12, 2001

(65) Prior Publication Data

US 2003/0113332 A1 Jun. 19, 2003

(51) Int. Cl.
C12N 5/16 (2006.01)
C12N 5/26 (2006.01)
C07K 16/28 (2006.01)

(52) U.S. Cl. .................... 435/331; 435/334; 435/343.1; 435/344.1; 435/348; 530/388.1; 530/388.22; 530/388.73; 530/388.85

(58) Field of Classification Search ............. 435/70.21, 435/331, 334, 343.1, 346, 355, 344.1, 348; 530/387.1, 387.9, 388.1, 388.73, 388.22, 530/388.85
See application file for complete search history.

(56) References Cited

U.S. PATENT DOCUMENTS

| | | | |
|---|---|---|---|
| 4,554,101 A | 11/1985 | Hopp | |
| 5,440,013 A | 8/1995 | Kahn | |
| 5,446,128 A | 8/1995 | Kahn | |
| 5,475,085 A | 12/1995 | Kahn | |
| 5,618,914 A | 4/1997 | Kahn | |
| 5,670,155 A | 9/1997 | Kahn | |
| 5,672,681 A | 9/1997 | Kahn | |
| 5,674,976 A | 10/1997 | Kahn | |
| 5,710,245 A | 1/1998 | Kahn | |
| 5,770,387 A * | 6/1998 | Litwin et al. | |
| 5,840,833 A | 11/1998 | Kahn | |
| 5,859,184 A | 1/1999 | Kahn et al. | |
| 5,929,237 A | 7/1999 | Kahn | |
| 6,114,143 A * | 9/2000 | Eda et al. | |

FOREIGN PATENT DOCUMENTS

| WO | WO 99/63088 | * 12/1999 |
|---|---|---|
| WO | WO 01/46260 | * 6/2001 |

OTHER PUBLICATIONS

Coffey, A.J. et al., Host Response to EBV Infection in X-Linked Lymphoproliferative Disease Results From Mutations in an SH2-Domain Encoding Gene, Nature Genetics, vol. 20, pp. 129-135, Oct. 20, 1998.
Davis, S.J., et al., CD2 and the Nature of Protein Interactions Mediating Cell-Cell Recognition, Immunological Reviews, vol. 163, pp. 217-236, 1998.
Kato, Kazunori, et al., CD48 is a Counter-Receptor for Mouse CD2 and is Involved in T Cell Activation, J. Exp. Med., vol. 176, pp. 1241-1249, Nov. 1992.
Kumaresan, Pappanaicken R., et al., Structure of the Human Natural Killer Cell Receptor 2B4 Gene and Identification of a Novel Alternative Transcript, Immunogenetics Aug. 18, 2000.
Mathew, Porunellor A., et al., Cloning and Characterization of the 2B4 Gene Encoding A Molecule Associated With Non-MHC-Restricted Killing Mediated by Activated Natural Killer Cells and T Cells, The Journal of Immunology, vol. 151, pp. 5328-5337, Nov. 15, 1993.
Sayos, J. et al., The X-Linked Lymphoproliferative-Disease Gene Product SAP regulates Signals Induced Through the Co-Receptor SLAM, Nature, vol. 395, pp. 462-469, Oct. 1, 1998.
Sewell, William A. et al., The Human LFA-3 Gene is Located at the Same Chromosome Band as the Gene for its Receptor CD2, Immunogenetics, vol. 28, pp. 278-282, 1988.
Smith, Glenn M., Detection of a Soluble Form of the Leukocyte Surface Antigen CD48 in Plasma and its Elevation in Patients With Lymphoid Leukemias and Arthritis, Journal of Clinical Immunology, vol. 17, pp. 502-509, 1997.
Stepp, Susan E., et al., Gene Structure of the Murine NK Cell Receptor 2B4: Presence of Two Alternatively Spliced Isoforms With Distinct Cytoplasmic Domains, Eur. J. Immunol., vol. 29, pp. 2392-2399, 1999.
Tangye, Stuart G., et al., Cutting Edge: Human 2B4, an Activating NK Cell Receptor Recruits the Protein Tyrosine Phosphatase SHP-2 and the Adaptor Signaling Protein SAP, The Journal of Immunology, vol. 162, pp. 6981-6985, Jun. 15, 1999.
Van Der Merwe P. Anton, et al., Human Cell-Adhesion Molecule CD2 Binds CD58 (LFA-3) With a Very Low Affinity and an Extremely Fast Dissociation Rate but Does not Bind CD48 or CD59, Biochemistry, vol. 33, pp. 10149-10160, 1994.
Van Der Merwe, P. Anton, et al., The NH2-Terminal Domain of Rat CD2 Binds rat CD48 with a Low Affinity and Binding Does not Require Glycosylation of CD2, Eur. J. Immunol., Vol. 23, pp. 1373-1377, 1993.

(Continued)

*Primary Examiner*—Karen A. Canella
(74) *Attorney, Agent, or Firm*—Jackson Walker L.L.P.

(57) ABSTRACT

The present invention relates to nucleic acid molecules encoding cell surface receptors on immune cells and the characteristic peptides that comprise these receptors. More specifically, the present invention concerns the use of synthetic and recombinant peptides comprising natural killer ("NK") cell surface receptors. The synthetic and recombinant peptides are used to generate monoclonal antibodies that bind a specific NK cell surface receptor called CS1. The binding of the monoclonal antibody to the NK cell surface receptor leads to NK cell activation. In a particular embodiments of the present invention, the monoclonal antibodies are utilized in a method that inhibits the growth of tumor cells.

14 Claims, 9 Drawing Sheets

OTHER PUBLICATIONS

Weiss, A., et al., Signal Transduction by Lymphocyte Antigen Receptors, Cell, vol. 76, pp. 263-274, Jan. 28, 1994.

Vita, C., et al., Novel Miniproteins Engineered by the Transfer of Active Sites to Small Natural Scaffolds, Biopolymers, vol. 47, pp. 93-100, 1998.

Weisshoff, H., et al, Mimicry of Beta II-Turns of Proteins in Cyclic Pentapeptides With One and Without D-amino Acids, Eur. J. Biochem., vol. 259, pp. 776-788, 1999.

Johannesson, P., et al., Bicyclic Tripeptide Mimetics With Reverse Turn Inducing Properties, J. Med. Chem., vol. 42, pp. 601-608, 1999.

* cited by examiner

Figure 2

Peptides for mAb production

| | |
|---|---|
| 1 | CQNRNRERVDFP |
| 2 | CMEHGEEDVIY |
| 3 | CQEEYEEKKRVDICRE |

_US 7,041,499 B2_

SEQUENCE LISTING

```
<160> NUMBER OF SEQ ID NOS: 2

<210> SEQ ID NO 1
<211> LENGTH: 1083
<212> TYPE: DNA
<213> ORGANISM: Homo Sapiens
<300> PUBLICATION INFORMATION:
<301> AUTHORS: Boles,K.S. and Mathew,P.A.
<302> TITLE: Molecular cloning of CS1, a novel human natural killer cell
<303> JOURNAL: Immunogenetics
<304> VOLUME: 52
<305> ISSUE: (3-4)
<306> PAGES: 302-307
<307> DATE: 2001
<308> DATABASE ACCESSION NUMBER: AF291815
<309> DATABASE ENTRY DATE: 2000-08-01
<313> RELEVANT RESIDUES: (1)..(1083)
<300> PUBLICATION INFORMATION:
<308> DATABASE ACCESSION NUMBER: AF291815
<309> DATABASE ENTRY DATE: 2000-08-01
<313> RELEVANT RESIDUES: (1)..(1083)

<400> SEQUENCE: 1
cagagagcaa tatggctggt tccccaacat gcctcaccct catctatatc ctttggcagc      60
tcacagggtc agcagcctct ggacccgtga aagagctggt cggttccgtt ggtggggccg     120
tgactttccc cctgaagtcc aaagtaaagc aagttgactc tattgtctgg accttcaaca     180 caaccctct tgtcaccata cagccagaag ggggcactat catagtgacc caaaatcgta     240
atagggagag agtagacttc ccagatggag gctactccct gaagctcagc aaactgaaga     300
agaatgactc agggatctac tatgtgggga tatacagctc atcactccag cagccctcca     360
cccaggagta cgtgctgcat gtctacgagc acctgtcaaa gcctaaagtc accatgggtc     420
tgcagagcaa taagaatggc acctgtgtga ccaatctgac atgctgcatg gaacatgggg     480
aagaggatgt gatttatacc tggaaggccc tggggcaagc agccaatgag tcccataatg     540
ggtccatcct ccccatctcc tggagatggg gagaaagtga tatgaccttc atctgcgttg     600
ccaggaaccc tgtcagcaga aacttctcaa gccccatcct tgccaggaag ctctgtgaag     660
```

-continued

```
gtgctgctga tgacccagat tcctccatgg tcctcctgtg tctcctgttg gtgcccctcc    720
tgctcagtct ctttgtactg gggctatttc tttggtttct gaagagagag agacaagaag    780
agtacattga agagaagaag agagtggaca tttgtcggga aactcctaac atatgccccc    840
attctggaga gaacacagag tacgacacaa tccctcacac taatagaaca atcctaaagg    900
aagatccagc aaatacggtt tactccactg tggaaatacc gaaaaagatg gaaaatcccc    960
actcactgct cacgatgcca gacacaccaa ggctatttgc ctatgagaat gttatctaga   1020
cagcagtgca ctgcccctaa gtctctgctc aaaaaaaaaa caattctcgg cccaaagaaa   1080
aca                                                                 1083
```

<210> SEQ ID NO 2
<211> LENGTH: 335
<212> TYPE: PRT
<213> ORGANISM: Homo Sapens
<300> PUBLICATION INFORMATION:
<301> AUTHORS: Boles,K.S. and Mathew,P.A.
<302> TITLE: Molecular cloning of CS1, a novel human natural killer cell
<303> JOURNAL: Immunogenetics
<304> VOLUME: 52
<305> ISSUE: (3-4)
<306> PAGES: 302-307
<307> DATE: 2001
<308> DATABASE ACCESSION NUMBER: AAK11549
<309> DATABASE ENTRY DATE: 2001-08-01
<313> RELEVANT RESIDUES: (1)..(335)
<300> PUBLICATION INFORMATION:
<308> DATABASE ACCESSION NUMBER: AAK11549
<309> DATABASE ENTRY DATE: 2001-08-01
<313> RELEVANT RESIDUES: (1)..(335)

<400> SEQUENCE: 2

```
Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205
```

```
-continued

Ile Leu Ala Arg Lys Leu Cys Glu Gly Ala Ala Asp Asp Pro Asp Ser
    210             215             220

Ser Met Val Leu Leu Cys Leu Leu Leu Val Pro Leu Leu Leu Ser Leu
225                 230                 235                 240

Phe Val Leu Gly Leu Phe Leu Trp Phe Leu Lys Arg Glu Arg Gln Glu
                245             250                 255

Glu Tyr Ile Glu Glu Lys Lys Arg Val Asp Ile Cys Arg Glu Thr Pro
            260             265             270

Asn Ile Cys Pro His Ser Gly Glu Asn Thr Glu Tyr Asp Thr Ile Pro
        275             280             285

His Thr Asn Arg Thr Ile Leu Lys Glu Asp Pro Ala Asn Thr Val Tyr
    290             295             300

Ser Thr Val Glu Ile Pro Lys Lys Met Glu Asn Pro His Ser Leu Leu
305             310             315             320

Thr Met Pro Asp Thr Pro Arg Leu Phe Ala Tyr Glu Asn Val Ile
                325             330             335
```

IMMUNO ACTIVATION OF CS1 RECEPTOR IN NATURAL KILLER CELLS TO INHIBIT TUMOR CELL GROWTH

BACKGROUND

The present invention relates to nucleic acid molecules encoding cell surface receptors on immune cells and the characteristic peptides that comprise these receptors. More specifically, the present invention concerns the use of synthetic and recombinant peptides comprising natural killer ("NK") cell surface receptors. The synthetic and recombinant peptides are used to generate monoclonal antibodies that bind a specific NK cell surface receptor called CS1. The binding of the monoclonal antibody to the NK cell surface receptor leads to NK cell activation. In a particular embodiments of the present invention, the monoclonal antibodies are utilized in a method that inhibits the growth of tumor cells.

The immune system is comprised of millions of cells including peripheral blood lymphocytes, monocytes and polymorphonuclear leukocytes, numerous soluble chemical mediators (cytokines and growth factors), and several lymphoid organs including thymus, postnatal bone marrow, lymph nodes, liver and spleen. All of these components work together through a complex communication system to fight against microbial invaders such as bacteria, viruses, fungi and parasites, and against newly arising malignant (tumor) cells. Natural killer ("NK") cells comprise a subset of peripheral blood lymphocytes that mediate a variety of functions that are important in human health and disease. Initial studies of NK cells concentrated on their ability to kill tumor cells, but like other lymphocytes, NK cells are now appreciated as having a broader role in the first line of host defense against invading pathogens, especially in the earliest phases of host immune responses.

NK-cell activity does not require prior exposure to the pathogen or in vivo clonal expansion, in contrast to the amplified response by cells in the specific effector arm of the immune system (B and T cells). Amplification by clonal expansion requires significant time, usually days to weeks. By then a host may succumb to certain pathogenic infections. NK cells are not static participants in host defense. Although NK cells are not effective against all viruses (for example, they have a less significant role in immune defense against influenza and lymphocytic choriomeningitis virus, even though infection can stimulate NK-cell activity), these cells have been shown to accumulate at sites of viral replication where they produce and release several cytokines such as gamma interferon (IFN-γ), tumor necrosis factor alpha (TNF-α), and the hematopoietic colony stimulating factors (CSFs) granulocyte-macrophage (GM)-CSF and interleukin-3 (IL-3). It is not yet known why NK cells are effective against certain pathogens and not others, but there is some evidence to suspect that there may be tissue-specific differences in dominant immune responses. Moreover, the mechanisms by which NK cells mediate their antiviral effects are not clearly understood.

Although not wanting to be bound by theory, the cytolytic function of NK cells and cytokine production are regulated by a delicate balance between signaling through activating and inhibitory receptors. Previous attention in the field has focused on MHC-recognizing receptors that are mostly inhibitory. However, one emerging group of activating NK cell receptors encompasses cell surface molecules of the Ig superfamily homologous to CD2. Although members of the CD2 subset of receptors do not recognize MHC molecules, they still play a major role in NK- and T-cell functions. Two members of this CD2 subset, 2B4 (CD244) and SLAM (CD150) receptors are involved in cellular activation such as lymphoproliferation, cytokine production, cytotoxicity, and invasiveness. The cytoplasmic domains of these transmembrane proteins contain novel tyrosine motifs (T-x-Y-x-x-I/V/A), which differ from those observed in other NK- and T-cell receptors. Another member of the CD2 subset, called CD84, also contains a consensus tyrosine motif, but its function remains unknown. The CD2 subfamily members bind homophilically to other members of the CD2 receptor subfamily, which is unlike the NK-cell receptors that bind MHC class I molecules (Davis et al. 1998). For example, CD2 receptor binds the CD58 receptor and both human and rodent CD48 receptors (Kato et al. 1992; van der Merwe et al. 1993, 1994). The CD48 is a high-affinity ligand for 2B4 and is widely expressed in leukocytes with its soluble form elevated in the blood of patients with lymphoid leukemias and arthritis (Smith et al. 1997). Additionally, the SLAM receptor is a self-ligand that activates T- and B-cells.

The tyrosine motifs in the SLAM and 2B4 receptors interact with a src homology 2 (SH2) domain of a SLAM-associated protein (SAP)/SH2D1A that is believed to stimulate a cytotoxic signaling pathway of the receptor (Sayos et al. 1998; Tangye et al. 1999). NK cells derived from SAP deficient individuals are no longer activated through 2B4. SAP is also essential for the signal transduction of other CD2 family receptors that are differentially expressed on cytotoxic lymphocytes. The lack of function of all these receptors in SAP-deficient individuals results in a complex deficit of NK, T and B cell responses that leads to un controlled infections. Mutations in the SH2 domain of SAP/SH2D1A have been identified as the genetic basis for X-linked lymphoproliferative disease (XLP) (Coffey et al. 1998; Nichols et al. 1998; Sayos et al. 1998). The 2B4 receptor transduces inhibitory signals in XLP patients when stimulated by CD48-positive B cells. Although not wanting to be bound by theory, these data suggest that the cause of XLP is complex and probably due to dysregulation of phosphorylation-dependent interactions at multiple sites, including the receptors and cytoplasmic adaptor molecules. In addition to the 2B4 and SLAM receptors, other receptors that contain the unique tyrosine motif might also contribute to the immune dysregulation seen in XLP.

In an attempt to identify novel cell surface receptors potentially involved in controlling cytolytic function we have identified, cloned and characterized a new member of the CD2 subset of receptors. We have named this new cell surface receptor CS1. This CS1 receptor is localized to the long arm of human Chromosome (Chr) 1 between CD48 and Ly-9 (CD229) and contains two of the unique tyrosine motifs. Disregulated signaling via the CS1 receptor may also contribute to the phenotype of XLP.

SUMMARY

The present invention relates to nucleic acid molecules encoding cell surface receptors on immune cells and the characteristic peptides that comprise these receptors. More specifically, the present invention concerns the use of synthetic and recombinant peptides comprising natural killer ("NK") cell surface receptors. The synthetic and recombinant peptides are used to generate monoclonal antibodies that bind a specific NK cell surface receptor called CS1. The binding of the monoclonal antibody to the NK cell surface receptor leads to NK cell activation. In a particular embodiments of the present invention, the monoclonal antibodies are utilized in a method that inhibits the growth of tumor cells.

One embodiment of the present invention relates to an isolated nucleic acid molecule comprising a nucleic acid sequence encoding a single trans-membrane 335 amino acid peptide that is a subset of the CD2 family of receptors, called the CS1 receptor. Stimulation of the CS1 cell surface receptor located on NK cells has been shown to activate the NK cells. Accordingly, another embodiment of the present invention utilizes synthetic and recombinant CS1 peptides as antigens to immunized mice to produce antibodies directed toward the CS1 receptor. The spleen cells of the immunized mice are used to generate hybrodoma cell lines that produce monoclonal antibodies specific for the CS1 cell surface receptors. Another embodiment of the present invention involves the use of the monoclonal antibodies that are directed toward the CS1 cell surface receptors on NK cell. Contacting an effective amount of the monoclonal antibody with natural killer cells will lead to their activation, and subsequent inhibition of tumor cell growth.

BRIEF DESCRIPTION OF THE DRAWINGS

FIG. 2 shows the alignment of amino acid sequences of CS1 and related receptors in the CD2 subset. Residues identical to CS1 are shaded and glycosylation sites are boxed. The amino acid comparison was compiled using the PILEUP program in the Genetics Computer Group software. A) Alignment of the extracellular domains. B) Alignment of the transmembrane domains. C) Alignment of the intracellular domains

FIG. 7 shows a table of the amino acid of the CS 1 fragments used to generate antibodies in the mice, wherein peptide 1 comprises SEQID#3, peptide 2 comprises SEQID#4, and peptide 3 comprises SEQID#5.

DETAILED DESCRIPTION OF PREFERRED EMBODIMENTS

Figure 1:
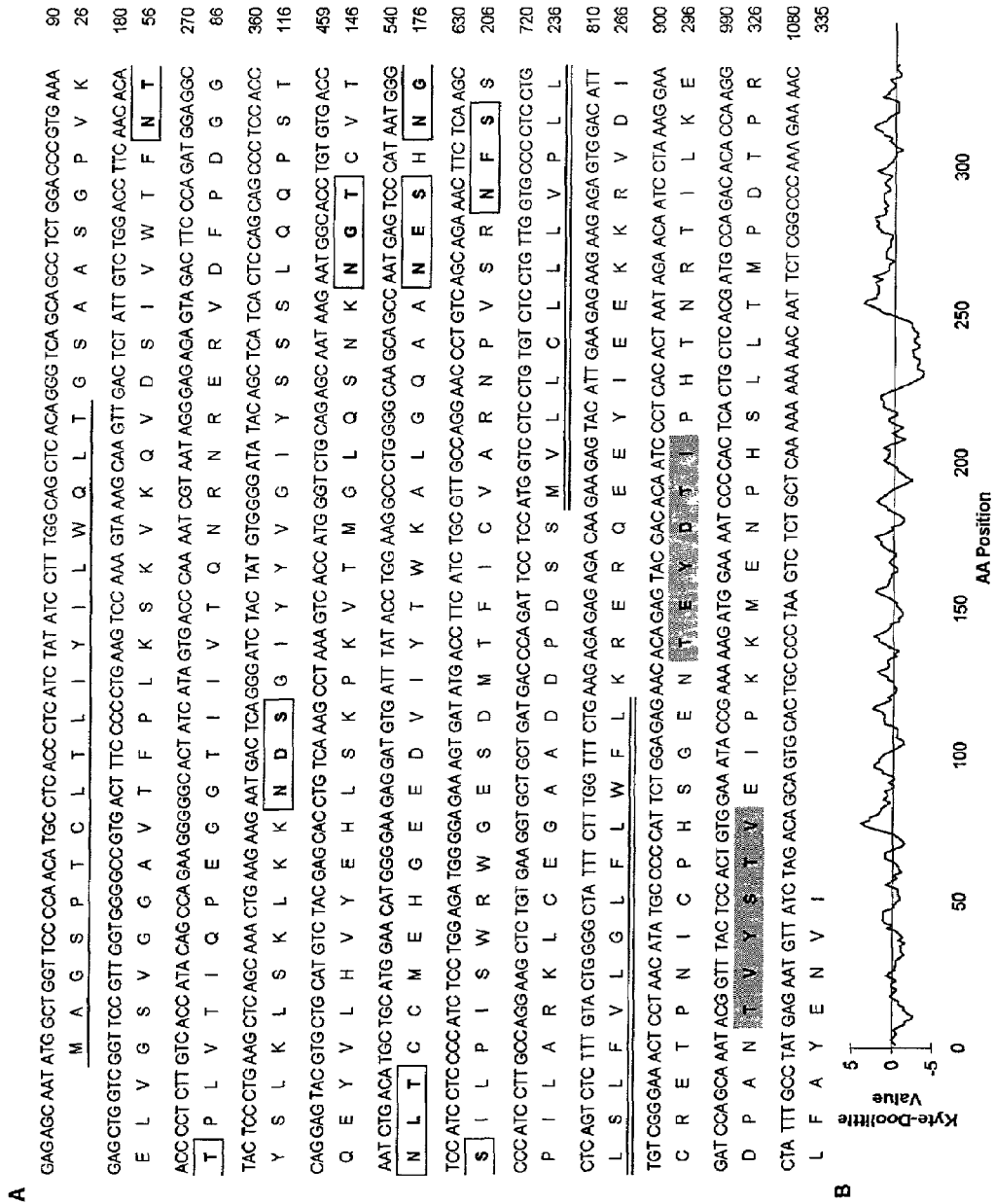
FIG. 1 shows the nucleotide sequence of CS1 cDNA and the predicted amino acid sequence. A) The nucleotide sequence and the putative peptide of CS1 (GenBank accession number AF291815). The signal peptide is underlined. The transmembrane domain is double underlined. Glycosylation sites in the extracellular domain are boxed. Tyrosine-containing motifs in the intracellular domain are shaded. B) Hydrophilicity plot of the CS1 putative peptide sequence determined by the Kyte-Doolittle method

General terms:

The term "nucleic acid expression construct" as used herein refers to any type of genetic construct comprising a nucleic acid coding for a RNA capable of being transcribed. The term "expression vector" can also be used interchangeably.

The term "functional biological equivalent" as used herein is a polypeptide that has been engineered to contain a distinct amino acid sequence while simultaneously having similar or improved biologically activity when compared to the peptide of SEQ NO. (1).

The term "subject" as used herein refers to any species of the animal kingdom.

The term "animal" as used herein refers to any species of the animal kingdom.

The term "promoter" as used herein refers to a sequence of DNA that directs the transcription of a gene.

The term "coding region" as used herein refers to any portion of the DNA sequence that is transcribed into messenger RNA (mRNA) and then translated into a sequence of amino acids characteristic of a specific polypeptide.

The term "heterologous nucleic acid sequence" as used herein is defined as a DNA sequence consisting of differing regulatory and expression elements.

The term "vector" as used herein refers to any vehicle that delivers a nucleic acid into a cell or organism. Examples include plasmid vectors, viral vectors, liposomes, or cationic lipids.

The term "catalytic antibody" as used herein refers an antibody that accelerates stimulation of immune cells.

The present invention relates to nucleic acid molecules encoding cell surface receptors on immune cells and the characteristic peptides that comprise these receptors. More specifically, the present invention concerns the use of synthetic and recombinant peptides comprising natural killer ("NK") cell surface receptors. The synthetic and recombinant peptides are used to generate monoclonal antibodies that specifically bind a specific NK cell surface receptor called CS1. The binding of the monoclonal antibody to the NK cell surface receptor leads to NK cell activation. In a particular embodiments of the present invention, the monoclonal antibodies are utilized in a method that inhibits the growth of tumor cells.

The immune system is comprised of millions of cells including peripheral blood lymphocytes, monocytes and polymorphonuclear leukocytes, numerous soluble chemical mediators (cytokines and growth factors), and several lymphoid organs including thymus, postnatal bone marrow, lymph nodes, liver and spleen. All of these components work together through a complex communication system to fight against microbial invaders such as bacteria, viruses, fungi and parasites, and against newly arising malignant (tumor) cells. Natural killer ("NK") cells comprise a subset of peripheral blood lymphocytes that mediate a variety of functions that are important in human health and disease. Initial studies of NK cells concentrated on their ability to kill tumor cells, but like other lymphocytes, NK cells are now appreciated as having a broader role in the first line of host defense against invading pathogens, especially in the earliest phases of host immune responses. The activation of NK cells probably results from the concerted action of cytokine receptors, adhesion molecules, and interactions between activating receptors recognizing ligands on the surface of tumors or pathogen infected cells. Upon activation, NK cells undergo blastogenesis, cytokine production, cytotoxicity, and migration.

Upon activation NK cells have been shown to produce and release several cytokines such as gamma interferon (IFN-γ), tumor necrosis factor alpha (TNF-α), and the hematopoietic colony stimulating factors (CSFs) granulocyte-macrophage (GM)-CSF and interleukin-3 (IL-3). Although not wanting to be bound by theory, the cytolytic function of NK cells and cytokine production are regulated by a delicate balance between signaling through activating and inhibitory receptors. Previous attention in the field has focused on MHC-recognizing receptors that are mostly inhibitory. However, one emerging group of activating NK cell receptors encompasses cell surface molecules of the Ig superfamily ("IgSF").

The IgSF domain is the most highly represented domain type, found in 34% of the leukocyte surface proteins. Of these, 45% have extra cellular regions comprised of two IgSF domians. Most of the IgSF members are involved in processes such as adhesion, migration, proliferation, differentiation, and effector functions of leukocytes Based on the structural features, chromosomal colocalization and evolutionary relationship, the IgSF family members subdivided into many groups and CD2 is one among them. The CD2 subfamily members includes the CD2, CD48, CD58, CD244 (2B4), CD150 (SLAM) and LY-9 molecules. The extracellular domain of the CD2 subfamily have similar patterns of the conserved disulfide bonds and typically comprise one membrane distal V-set domain and one membrane-proximal C2-set domain, with exception of Ly-9, which contains a tandem repeat of V-C2 set domains. The genes that encode CD2 family members are located on human chromosome 1 in two complexes. 2B4, SLAM, CD48, CS1, LY9 and CD84 are located on the long arm 1q21-24 and homologous mouse genes are located on the syntenic region of mouse chromosome 1. In contrast, CD2 and CD58 are located in the short arm 1p13 of human chromosome 1 and mouse chromosome 3.

Members of the CD2 members play a major role in lymphocyte functions and do not recognize MHC molecules. CD2 and CD58 interaction is important for T cell mediated cytotoxicity, antigen- and mitogen-induced T cell proliferation, and lymphokine production. CD150 is expressed on T cells and B cells and regulates T cell activation and production of Ig by B cells.

EXAMPLE 1

Cloning and Characterization of the CS1 Receptor Clone

In an attempt to identify novel cell surface receptors potentially involved in controlling cytolytic function we have cloned and characterized CD244 (2B4), which as an activation receptor on human NK cells and mouse NK cells and T cells that are involved in non-MHC-restricted killing. In addition, we have cloned and characterized a new member of the CD2 subset of receptors. We have named this new cell surface receptor CS1. This CS1 receptor of the present inventention is localized to the long arm of human Chromosome (Chr) 1 between CD48 and Ly-9 (CD229) and contains two of the unique tyrosine motifs.

To identify the CS1 receptor we searched the expressed sequence tag (EST) database at GenBank with the TblastN program versus a consensus sequence of human members of the CD2 subset. Several overlapping clones were identified and oligonucleotide primers were designed to amplify a 363-bp fragment within the cytoplasmic domain. cDNA from an NK-cell library constructed in λ phage by Dr. J. Houchins (R & D Systems, Minneapolis, Minn., and kindly provided by Dr. A. Brooks, NIH, Bethesda, Md.) was successfully used as template. PCR cycle conditions were 94° C. for 30 seconds, 50° C. annealing temperature for 30 seconds, and a 72° C. extension for 45 seconds repeated for 30 cycles using Taq DNA polymerase from Gibco-BRL (Grand Island, N.Y.) at 2 mM $MgCl_2$. The same library was subsequently screened with the resulting PCR fragment labeled with $\alpha^{32}$P-dCTP. Approximately $5\times10^5$ clones were hybridized. After three rounds of screening, phage DNA was isolated from positive clones and sequenced (Automated Sequencing Facility, Department of Pathology, UT Southwestern Medical Center, Dallas, Tex.).

Figure 2:
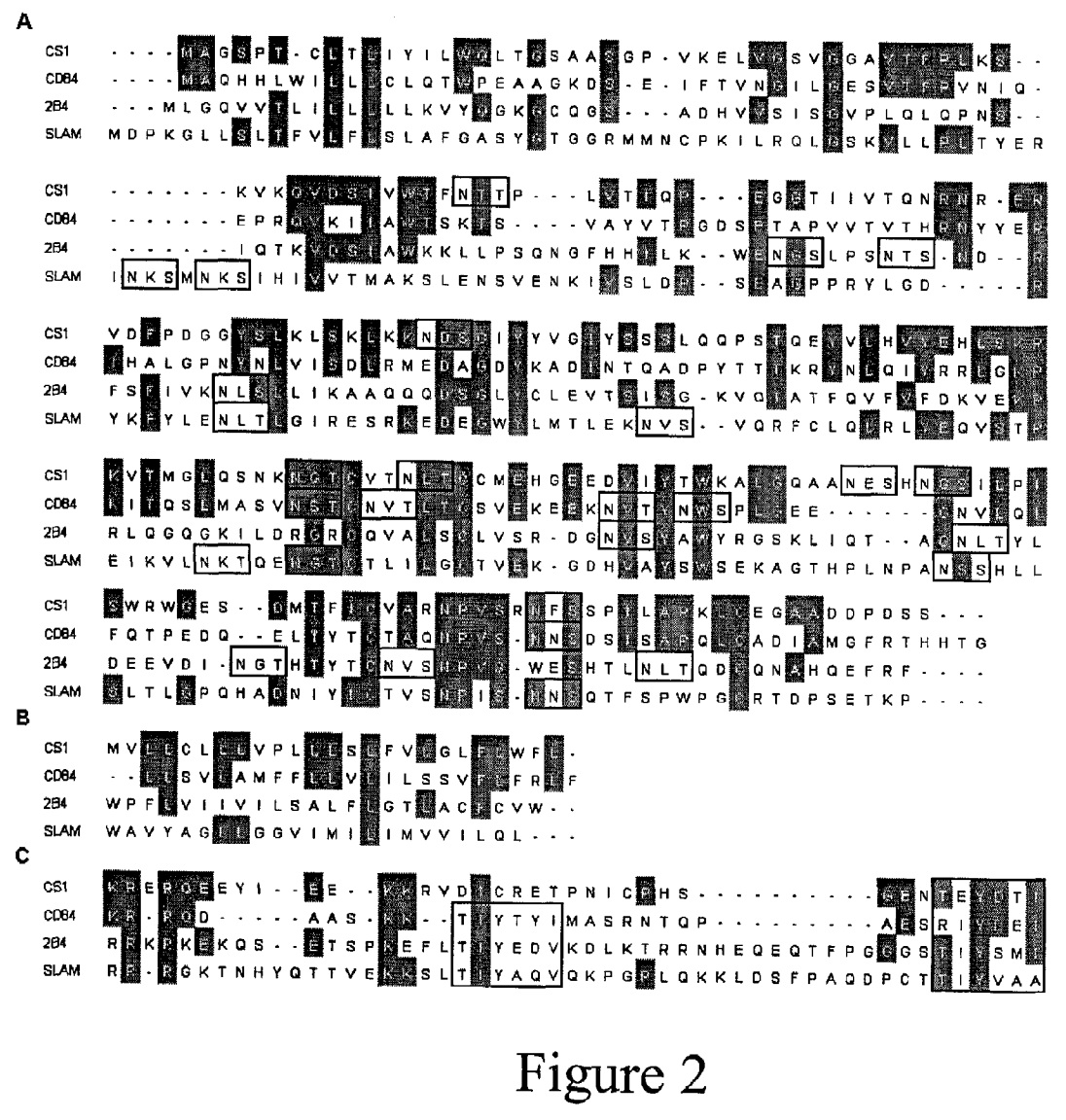

One of the clones (C9C1A), with a cDNA insert of 1083 bp, contained an open reading frame encoding a polypeptide of 335 amino acid residues (GenBank accession number AF291815). The transcript was named CS1 (CD2 subset 1) due to its similarity to other members of the CD2 subset of receptors. The predicted protein sequence had a single transmembrane domain of 25 amino acid residues (FIGS. 1A, B) and an intracellular domain of 85 amino acid residues. Additionally, it had an extracellular domain of 225 amino acid residues which contained seven putative N-linked glycosylation sites (FIG. 1A). The homology of the predicted protein sequence of CS1 indicates that it is a member of the Ig superfamily. Furthermore, it is a new member of the CD2 subset of receptors. It has the highest homology to CD84, SLAM, and 2B4 with 47, 44, and 40% similarity, respectively (FIG. 2). Alignment of the CS1 putative protein indicates a similar structure with many conserved residues compared to other CD2 subset receptors. The cytoplasmic region contains two of the novel tyrosine motifs observed in 2B4 and SLAM. These are indicated by a threonine residue in the −2 position relative to the tyrosine (T-x-Yxx-I/V/A). There is an additional tyrosine-containing motif near the C-terminal of the CS1 receptor. The −2 position of that motif is phenylalanine (F-x-Y-x-x-V) and is therefore not a consensus motif.

Figure 3:
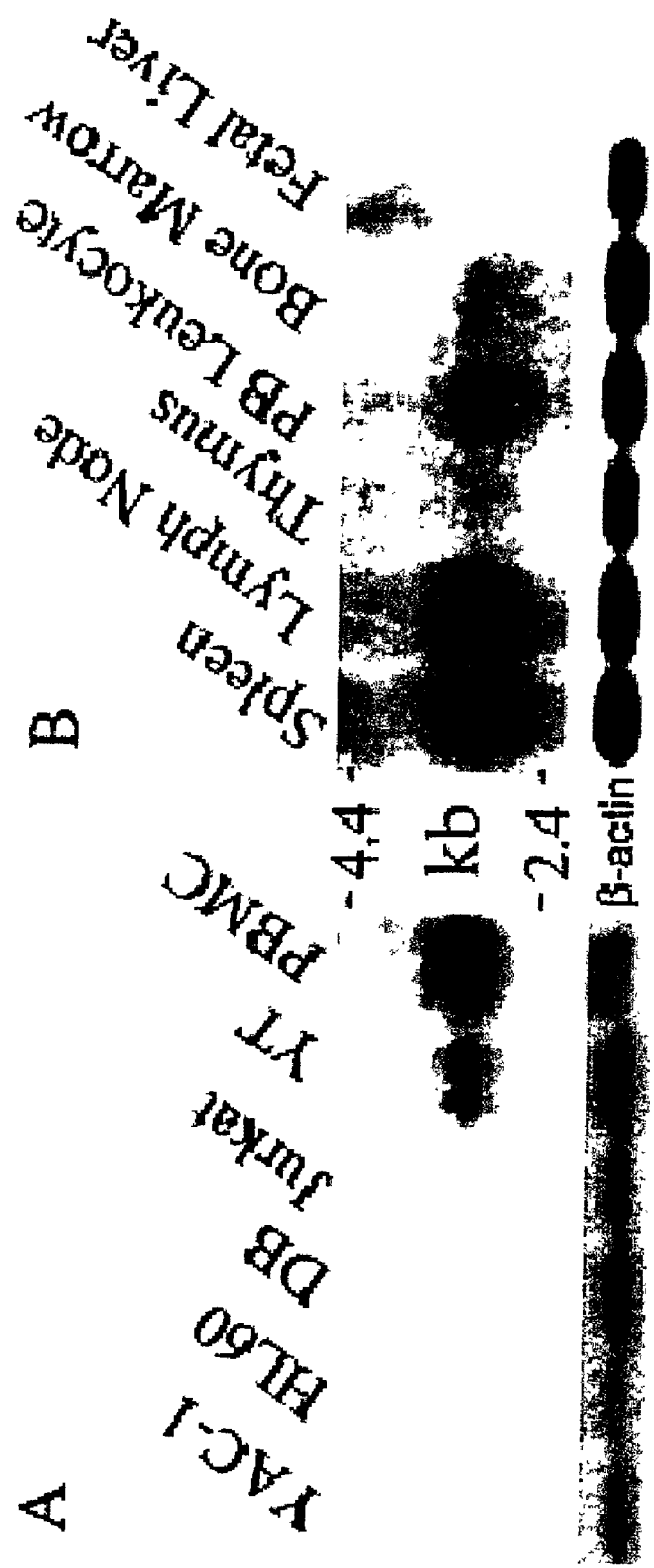
FIG. 3 shows an RNA blot analysis of the CS1 transcript hybridized with 32 P-labeled, full-length CS1 cDNA. Both membranes were stripped and hybridized with a-actin probe. The positions of the RNA molecular standards are shown in the center. A) A membrane containing total RNA (20 μg) isolated from the YAC-1, HL-60, DB, Jurkat, and YT tumor cell lines. Additionally, a sample was included from the PBMCs of a healthy donor. B) Northern blot of poly(A)+ RNA from spleen, lymph node, thymus, peripheral blood leukocytes, bone marrow, and fetal liver tissues. The membrane was a Human Immune System Multiple Tissue Northern Blot II purchased from Clontech (Palo Alto, Calif.)

Expression of the CS1 transcript in various cell lines and different human tissues was analyzed by northern blotting of total RNA and poly(A)+RNA. Human tumor cell lines Jurkat (T cell), YT (NK cell), HL-60 (promyelocytic), and DB (B cell), in addition to a mouse lymphoma cell line (YAC-1), were cultured in RPMI 1640 supplemented with 10% FCS (Hyclone, Logan, Utah), 2 mM L-glutamine, 100 units/ml of penicillin and streptomycin, 1 mM sodium pyruvate, and 0.1 mM nonessential amino acids (Gibco-BRL). All cell lines were grown to $1 \times 10^6$/ml and split 1:2 24 h before RNA isolation. PBMCs were isolated from 60 ml of venous blood from a healthy donor by Ficol-Paque centrifugation (Pharmacia, Piscataway, N.J.). Total RNA was isolated with the RNAstat 60 reagent according to the manufacturer's protocol (Teltest, Friendswood, Tex.), divided into 20-µg aliquots, and stored in 70% EtOH at −80° C. until use. Northern blots were probed with 25 ng of the full-length cDNA labeled with $^{32}$P-dCTP. The first blot consisted of 20 µg of total RNA from human promyelocytic, T-, B-, and NK-cell lines (HL-60, Jurkat, DB, and YT, respectively), a mouse cell line (YAC-1), and PBMCs from a healthy donor immobilized on Hybond nylon (Amersham, Arlington Heights, Ill.). Hybridization was performed following the instructions of Amersham for the Hybond nylon membrane at 65° C. The second membrane was purchased from Clontech (Palo Alto, Calif.) and contained mRNA samples from human spleen, lymph node, thymus, peripheral blood leukocytes, bone marrow, and fetal liver (Human Immune System Multiple Tissue Northern Blot II). It was hybridized following the manufacturer's directions with the included ExpressHyb Hybridization solution at 65° C. Blots were exposed to Hyperfilm (Amersham). The membranes were subsequently stripped and reprobed for -actin (FIG. 3) to insure equal loading. The full-length cDNA hybridized to a transcript of approximately 3 kb in total RNA from both a human NK-cell line (YT) and PBMCs of a healthy donor (FIG. 3A). Tissue distribution of CS1 showed that human peripheral blood leukocytes, lymph node, and spleen expressed a transcript of the same relative size. Additionally, a weak signal was detected in bone marrow (FIG. 3B). The expression of the CS1 transcript in lymph node and spleen suggests that it may be expressed in other lymphocyte populations. The relative distribution and regulation of the transcript remains to be determined. Genes encoding members of the CD2 subset of receptors are on human Chr 1 (Tangye et al. 2000). CD2 and CD58 genes are located on the short arm of human Chr 1 at 1p13. 2B4, CD48, CD84, SLAM and Ly-9 have been localized to the long arm of Chr 1 at 1q21-24. A Blast search using the CS1 cDNA versus the human genomic databases at GenBank identified a 196-kb contiguous sequence containing the CS1 gene located on the long arm of Chr 1 at 1q23-24 (GenBank accession number AL121985).

Figure 4:
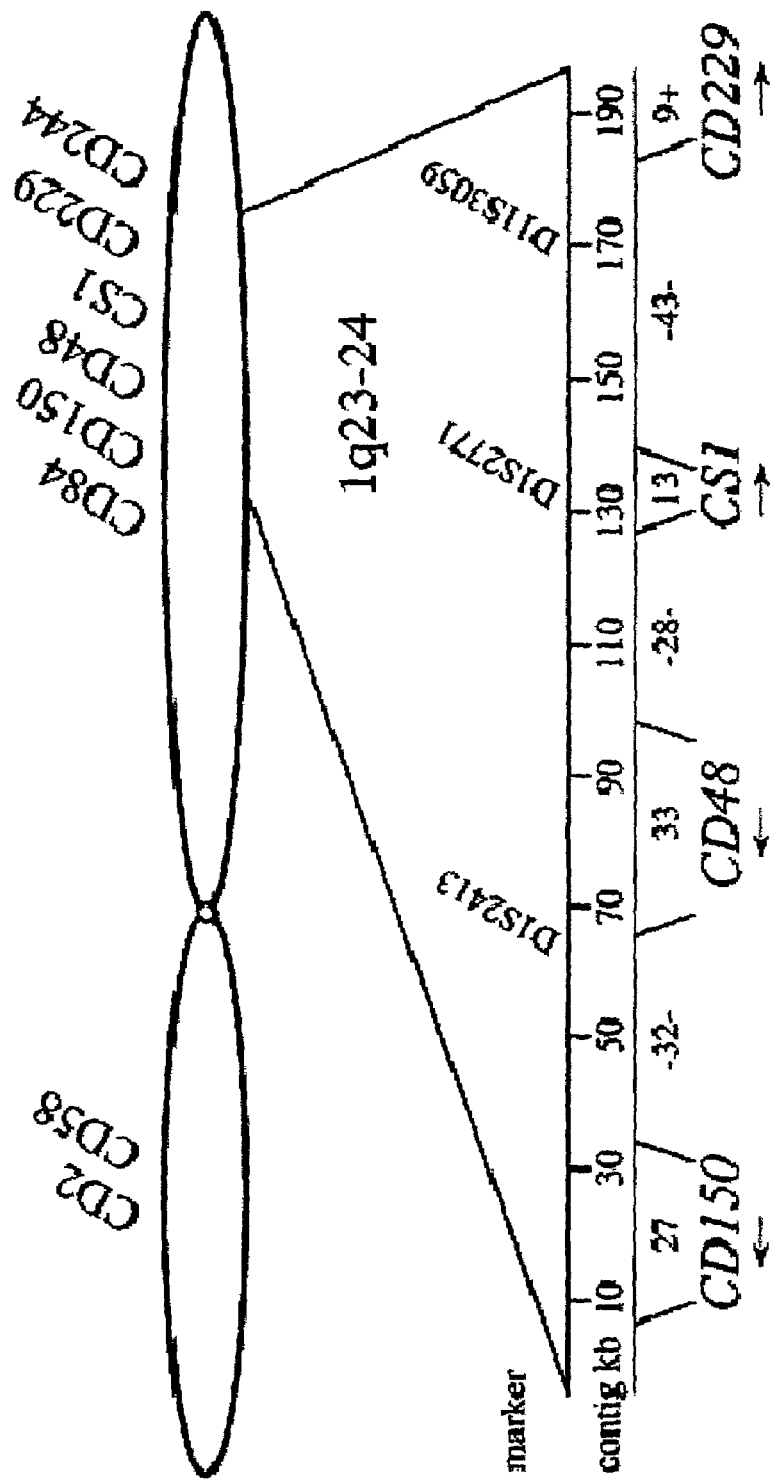
FIG. 4 shows the map of the CD2 subset of receptors located on human Chr 1. CD2 and CD58 are located on the short arm of Chr 1 at 1p13. CS1 is located on the long arm of Chr 1 at 1q23-24 along with CD48, CD84, CD150 (SLAM), CD229 (Ly-9), and CD244 (2B4). The inset showing the location of CS1 is based on analysis of a contiguous genomic sequence (GenBank accession number AL121985). Genetic markers are listed within the contiguous sequence in addition to the relative position of the genes in kilobases. Gene sizes and intragene spacing in kilobases are listed underneath. The arrows indicate relative gene orientation.

Analysis indicated that CS1 is located between CD48 and Ly-9 (FIG. 4). Furthermore, the contiguous sequence contained the SLAM gene and a portion of the Ly-9 gene. The genomic organization of both the mouse and human 2B4 genes has been characterized and they are relatively large at about 25 kb (Kumaresan and Mathew 2000; Stepp et al. 1999). Analysis of the CS1 gene sequence revealed a size of 13 kb. The size discrepancy compared to 2B4 is due to a smaller first intron of 8.7 kb in the CS1 gene as opposed to a 17-kb first intron in the 2B4 gene.

EXAMPLE 2

Production of Antibodies for CS1

The identification and characterization of the CS1 gene has important utility for the present invention that allowed the inventors to produce a synthetic or recombinant peptide that could be utilized for monoclonal antibody production toward the CS1 receptor. The approach was to prepare synthetic peptides of the CS1 receptor to use as antigens. Subsequently, the CS1 protein was produce as a fusion with a GST protein and expressed in a bacterial expression system and column purified. The resulting protein was used as antigen in the final boost.

Synthetic Peptide CS1 Production: The first approach was to prepare synthetic peptides of the CS1 receptor and inject these synthetic peptides into a mouse as an immunizing antigen. However, before specific peptide epitopes are produced, sequences were screened with programs that contain algorithms to predict the optimal antiginecity (e.g. MacVector™, Dastard, and PC-Gene$^e$). The selected peptides were synthesized and custom antibodies obtained by procedures that are common in the art.

Recombinant Peptide CS1 Production: The second approach was to prepare DNA expression constructs that contained open reading frames for the encoded peptides of the CS1 receptor. Following transfection of the DNA constructs into *E. coli* cells line, the peptides for the CS1 receptor can be isolated by methods known to persons with ordinary skill in the art. These recombinant peptides can then be injected these synthetic peptides into a mouse as an immunizing antigen.

Following the production of antigens directed toward CS1, in was necessary to develop a monoclonal antibody. The production of a hybridoma cell line from an antigen is well known in the art and the example outlined here is not intended to limit the scope of the invention. The production of a hybridoma cell line the includes the following three stages:

Stage I

Immunization—Virus and antibody-free mice are immunized with the specific antigen or proteionacious composition. In a preferred embodiment, the synthetic peptides of the CS1 receptor or the CS1-fusion protein described above are used. The mice are housed in an isolator during the immunization period. At six weeks, following the primary immunization and the first boost, the mice are tested for antibody titer. The antibody titer is determined by ELISA assay, alternative assays can be utilized. If additional boosts are needed, they are administered and the mice are retested for antibody titer. Once immunization is complete, the mice are held for three to four weeks before fusion. Three to five days before the fusion, a mouse will be selected for the pre-fusion boost.

Stage II

Fusion—The spleen from the mouse will be harvested and all spleen cells fused with a myeloma cell line. Six to ten 96-well panels for plating. Cells are grown in HAT selection medium. A maximum of three separate fusions will be performed.

Screen and Select—All 96-well panels are screened by ELISA for antibody positive wells. Fifty to one hundred positive wells are expanded and retested three to four days later by ELISA. The standard production is screened with a single ELISA antigen. Additional ELISA antigens can be added as an option. Typically less than 30 positive wells from the second assay are selected to be expanded for possible cloning. Cells from these positive wells are frozen as backup and 0.2 ml of tissue culture supernatant/clone used for further testing.

Stage III

First Cloning—Typically less than 15 positive wells are selected for cloning by the limiting dilution method. Isolated colonies are tested by ELISA, and positives selected to be expanded for the next cycle of cloning. Cells from these positive clones are frozen as backup.

Final Cloning—Approximately 12 positive clones from the first cloning cycle are selected for the second cycle. Isolated colonies are tested by ELISA, and positives selected to expand. Several cycles of cloning may be required in order to obtain true, stable clones. Cells from these positive clones are frozen as backup. The method of isolation of monoclonal antibodies from the positive hybridoma cell lines are well known in the art, and will not be discussed here.

EXAMPLE 2

The CS1 Receptor is Expressed on the Cell Surface of NK Cells.

A utility of the present invention to demonstrate that the CS1 receptor is expressed on the surface of NK cells. Thus, the inventors synthesized a fusion protein of the CS1 receptor with a FLAG peptide and utilized YT cells to test for the specific surface expression of CS1 with an antibody against the FLAG peptide.

Figure 5:
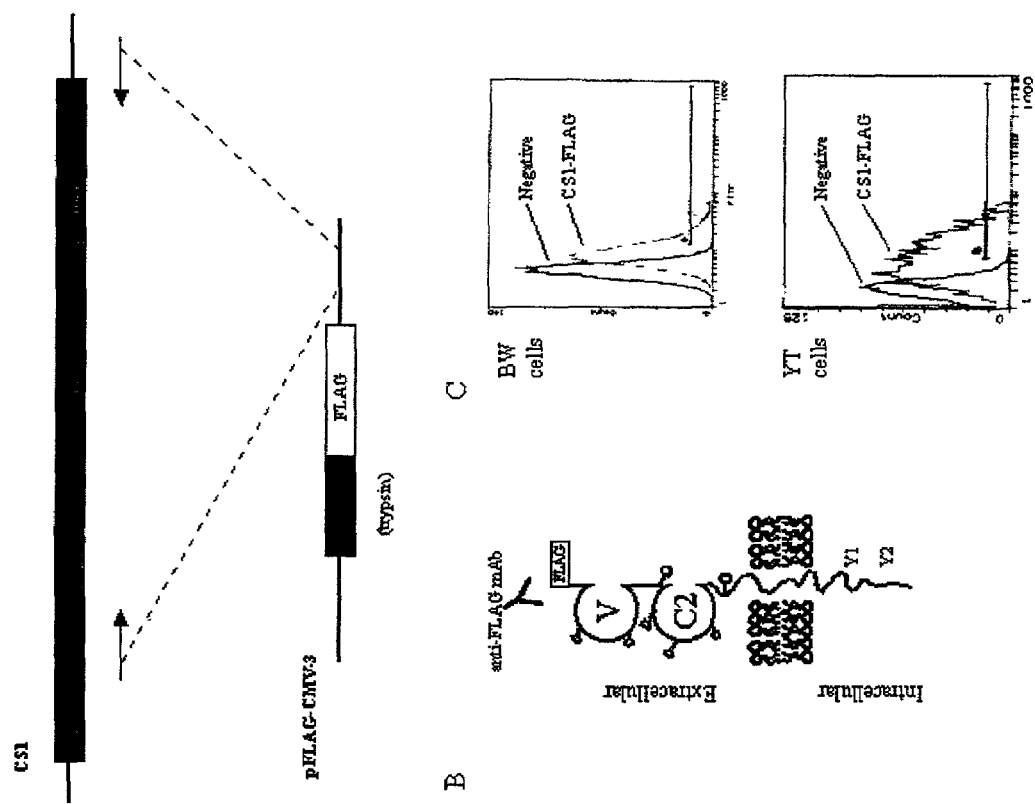
FIG. 5 shows a diagram of the construct to introduce a FLAG epitope into the N-terminal of the CS1 receptor A) Diagram of the CS1-FLAG construct. CS1 represents the cDNA. Arrows indicate the position of PCR primers used to amplify the cDNA without the leader sequence. pFLAG-CMV3 is the expression vector with a leader sequence (trypsin) and a FLAG epitope under the expression of a CMV promoter. The CS1 cDNA fragment was cloned in frame into the expression vector with EcoR I and Xba I sites that were introduced via the PCR primers. B) Diagram of the CS1/FLAG construct as expressed on the cell surface of a transfected cell. C. Flow cytometry of CS1/FLAG constructs expressed in the cancer cell lines, BW and YT.

A construct that introduced a FLAG epitope into the N-terminal of the CS1 receptor is shown in FIG. 5A. The diagram shows the CS1-FLAG DNA expression construct. The arrows indicate the position of PCR primers used to amplify the cDNA without the leader sequence. pFLAG-CMV3 is the expression vector with a leader sequence (trypsin) and a FLAG epitope under the expression of a CMV promoter. The CS1 cDNA fragment was cloned in frame into the expression vector with EcoR I and Xba I sites that were introduced via the PCR primers. A diagram of the CS1/FLAG construct as expressed on the cell surface of a transfected cell is shown in FIG. 5B. Furthermore, the expression of the CS1/Flag construct in the cancer cell lines, BW and YT is shown in FIG. 5C.

EXAMPLE 3

Assay for Lytic Activity of Cells by Stimulation of the CS1 Receptor with a CS1-Ig Fusion Protein.

Figure 6:
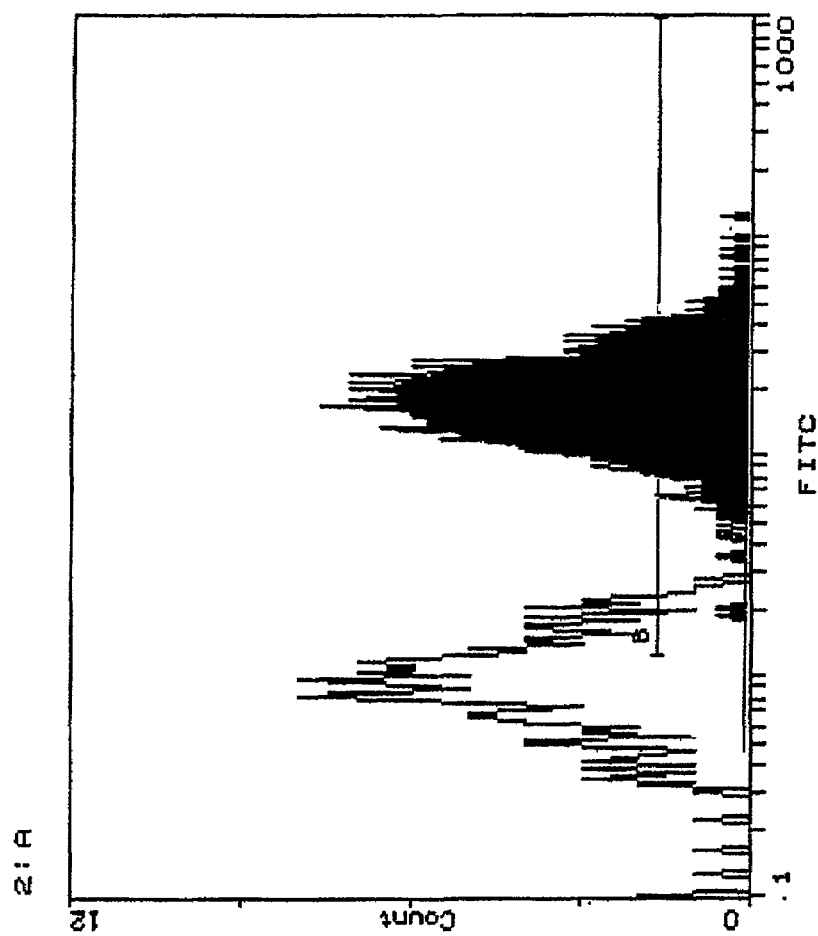
FIG. 6 CS1-Ig fusion protein used to stimulate natural killer cell cytotoxicity against tumor cell targets. CS1-Ig fusion protein binds B 16 melanoma cells trasfected with the full-length DNA for CS1. Only the transfected cells (black fill) showed labeling with the CS1-Ig fusion protein versus the non-trasfected cells (white fill). CS1-Ig fusion protein is a ligand for the CS1 receptor.

A utility of the present invention is to increase the lytic activity of NK cells toward tumor cells when the CS1 receptor stimulated with a monoclonal antibody or biological binding equivalent. Thus, the inventors synthesized a fusion protein of the CS1 receptor with a Ig peptide and utilized YT cells to test for the specific lytic activity of K562 target cells when the fusion protein CS1 receptor was stimulated in YT cells with the CS1-Ig fusion protein. A construct that introduced an Ig protein to the C-terminal of the CS1 receptor is shown in FIG. 6. The diagram shows the CS1-Ig DNA expression construct.

CS1-Ig fusion protein construct: The CS1-Ig fusion protein was made by fusing the CD5 leader peptide with V and C2 domain of the CS1 and with CH2 and CH3 regions of the human IgG1. The extra cellular domain of the CS1 was PCR amplified using forward primers corresponding to the sequences immediately downstream of the signal sequences cleavage site and containing a NheI site and the reverse primer immediately upstream of the transmembrane region and containing a Bam HI site. The amplified products were digested with NheI and BamHI and cloned into the NheI-BamHI cut pCD51neg1 mammalian expression vector. M2B4-hIgG was used as a control and following primers were used to amplify the extra cellular domain of the CS1. The CS1-hIgG fusion protein construct is shown in FIG. 6.

In order to produce a soluble CS1-hIgG fusion protein, the Cs1-hIgG plasmid was transiently transfected into B16 mouse melanoma cells using Figene-6 transfection reagent. Two days after the transfection, cells were labeled with a radioactive amino acid (e.g. $^{35}$S-Methonien—150 mCi/ml, Trans-label, ICN Biochemicals), for 4 hr and the supernatants were assayed for the presence of human immunoglobulin-containing proteins by precipitation with protein-A-agarose. The integrity of the purified protein was verified by SDS-PAGE. For large scale production of fusion proteins, serum-free medium was added in the transfected B16 cell line and the supernatant were collected on day 4, day 6 and day 8. The CS1-hIgG fusion protein was affinity purified on protein-A-agarose using Biorads MAPS kit.

Flow cytometry and CS1-IgG fusion protein binding assays were used to confirm fusion protein production. Mouse lymphoma cells were transfected with CD244 (2B4), CD48, CS1 and BLAME cDNAs using the Fugene transfection reagent (Roche pharmaceuticals). After 48 h of incubation, cells were incubated with mAbs or polyclonals against the CD244, CD48 and CS1 to detect the expression of the molecules. They were then washed with cold PBS and incubated with FITC conjugated anti-mouse secondary antibodies for 30 min at 4C. Samples were washed and measured by flow cytometer (Coulter flow cytometer). When CS1-IgG fusion protein binding was assayed, cells were incubated with a CS1-IgG fusion protein for 2 h at 4° C. They were washed with ice cold PBS at very low speed for three times. Cells were incubated in FITC-conjugated anti-human IgG secondary anti bodies for 30 min at 4° C. After three wash, the cells were immeadiately analyzed by FACS.

Figure 8:
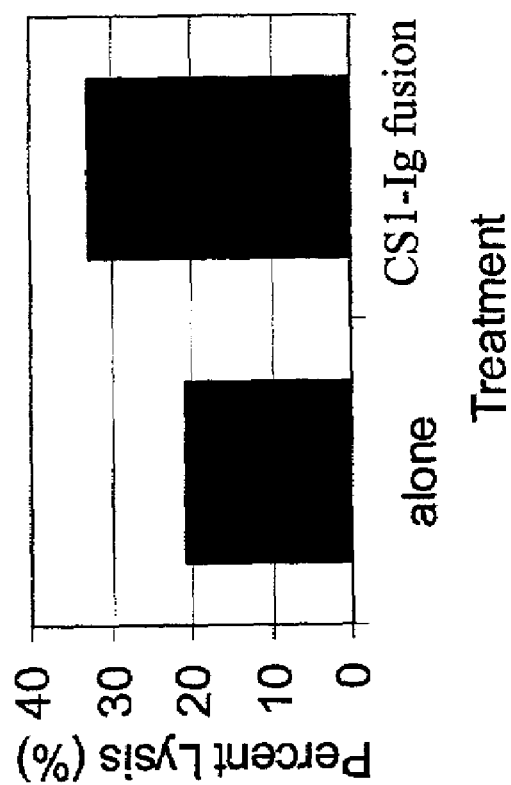
FIG. 8 shows how activated natural killer cells induce cytotoxicity in a tumor cell line. Cytolytic activity of the human NK cell line YT stimulated with the CS1-Ig fusion protein. Cytotoxicity was determined in a standard 4 hr 51Cr release assay. K562 cells were used as tumor targets in direct lysis by the YT cells.

YT cells were tested for specific lysis of K562 target cells in a 4 hr $^{51}$Cr release assay as is known by a person skilled in the art. The YT cells were incubated for 30 minutes with complete media alone or in addition to monoclonal antibodies in a 96 well, round bottom plate prior to the addition of $^{51}$Cr-laeled target cells. The CS1 receptor was used to stimulate the YT cells via the CS1-Ig fusion protein, and cells were subsequently incubated at 37° C. for four hours. The plates were spun at 250 ×g for 7 minutes to pellet the cells and 100 ul of the supernatant was removed and counted by scintillation counting. Percent cytotoxicity was calculated as described. Cytolytic activity of the human NK cell line YT. Cytotoxicity was determined in a standard 4 hr $^{51}$Cr release assay. As shown in FIG. 8, K562 cells represent direct lysis by the YT cells.

Figure 9:
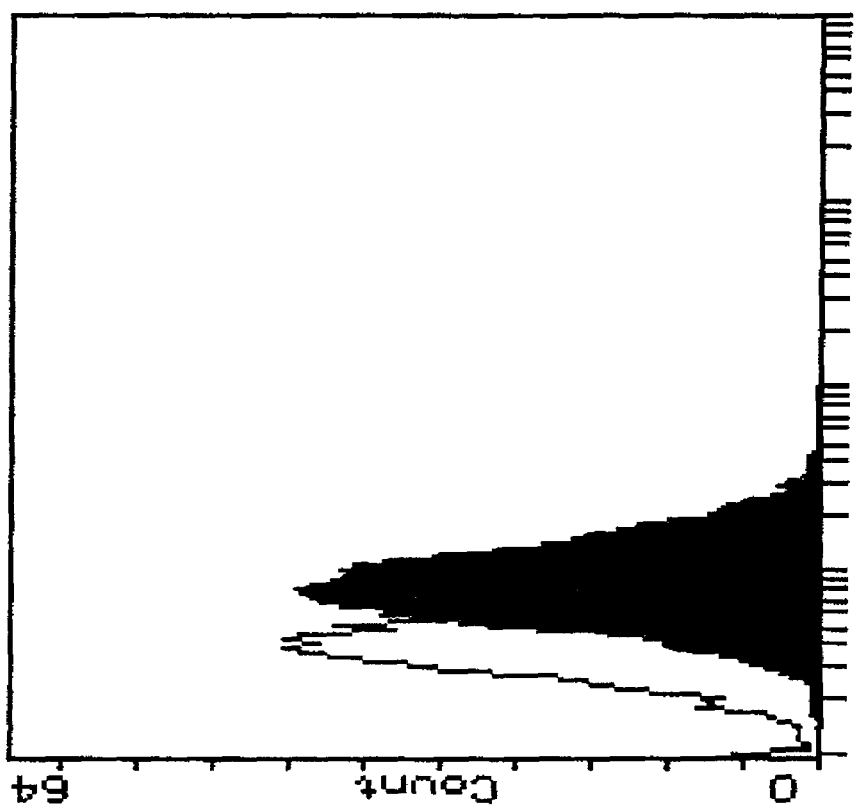
FIG. 9 shows the CS1 monoclonal antibody binds specifically to the CS1 receptor. The full-length CS1 receptor was expressed in the BW cell line. Only the transfected cells (black fill) showed labeling with the anti-CS1 monoclonal antibody versus the non-trasfected cells (white fill).

The CS1 monoclonal antibody binds specifically to the CS1 receptor. This was shown by expressing the fill-length CS1 receptor in the BW cell line. As shown in FIG. 9, only the transfected cells (black fill) showed labeling with the anti-CS1 monoclonal antibody versus the non-trasfected cells (white fill). Additionally, stimulation of the CS1 receptor with CS1-Ig fusion protein modulates IFN-γ secretion in YT cells.

Proteinaceous Compositions. In certain embodiments, the present invention concerns novel compositions comprising at least one proteinaceous molecule. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

As used herein, an "amino molecule" refers to any amino acid, amino acid derivitive or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid. Several examples of modified or unusual amino acids are listed in Table 1 below, however, this list only provides some examples and is not meant to limit the possiblilities of modified or unusual amino acids that could be used in a proteinaceous composition.

TABLE 1

Modified and Unusual Amino Acids

| Abbr. | Amino Acid |
|---|---|
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance which produces no significant untoward effects when applied to, or administered to, a given organism according to the methods and amounts described herein. Organisms include, but are not limited to any species in the animal kingdom. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. It is contemplated that antibodies to specific tissues may bind the tissue(s) and foster tighter adhesion of the glue to the tissues after welding. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject.

As modifications and/or changes may be made in the structure of the polynucleotides and and/or proteins according to the present invention, while obtaining molecules having similar or improved characteristics, such biologically functional equivalents are also encompassed within the present invention. One example as mentioned above are modified polynucleotides and polypeptides. The biological functional equivalent may also comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within ±0.5 are even more particularly preferred.

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multidisulfide-containing proteins as attractive structural templates for producing biologically active conformations that mimic the binding sites of large proteins. Vita et al. (1998). A structural motif that appears to be evolutionarily conserved in certain toxins is small (30–40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

The present invention includes the principle for the production of a monoclonal antibody directed against the cell surface receptor CS1. In addition, the present invention includes a method for inhibiting tumor cell growth utilization the monoclonal antibody described herein. Thus, it should be appreciated by those of ordinary skill in the art that other embodiments may incorporate the concepts, methods, antibodies, cell surface receptors, and devices of the above description and examples. The description and examples contained herein are not intended to limit the scope of the invention, but are included for illustration purposes only. It is to be understood that other embodiments of the invention can be developed and fall within the spirit and scope of the invention and claims.

What is claimed:

1. A monoclonal antibody produced by:
   (a) injecting an animal with a proteinaceous molecule to produce an immunized animal, wherein the proteinaceous molecule is (SEQID No.: 3), (SEQID No.: 4), or (SEQID No.: 5);
   (b) harvesting spleen cells from the immunized animal to give harvested spleen cells;
   (c) fusing the harvested spleen cells with an immortal cell line to produce a fusion cell line;
   (d) screening the fusion cell line to identify cells that specifically produce a monoclonal antibody with affinity toward (SEQID No.: 3), (SEQID No.: 4), or (SEQID No.: 5); and
   (e) selecting and expanding the fusion cell line only with cells that specifically produce the monoclonal antibody.

2. The monoclonal antibody of claim 1, wherein the immunized animal comprises a mouse.

3. The monoclonal antibody of claim 1, wherein the immortal cell line comprises a myeloma.

4. The monoclonal antibody of claim 1, wherein (SEQID No.: 3), (SEQID No.: 4), or (SEQIDNo.:5) is linked to an immunological adjuvant.

5. The monoclonal antibody of claim 1, wherein the (SEQID No.: 3), (SEQID No.: 4), or (SEQIDNo.:5) further comprises a fusion protein.

6. The monoclonal antibody of claim 5, wherein the fusion protein comprises (SEQID No.: 3), (SEQID No.: 4), or (SEQID No.: 5) fused to a Glutathione S Transferase ("GST") protein.

7. A fusion cell line produced by:
   (a) injecting an animal with a proteinaceous molecule to produce an immunized animal, wherein the proteinaceous molecule is (SEQID No.: 3), (SEQID No.: 4), or (SEQID No.:5);
   (b) harvesting spleen cells from the immunized animal to give harvested spleen cells;
   (c) fusing the harvested spleen cells with an immortal cell line to produce a fusion cell line;
   (d) screening the fusion cell line to identify cells that specifically produce a monoclonal antibody with affinity toward (SEQID No.: 3), (SEQID No.: 4) or (SEQID No.: 5); and
   (e) selecting and expanding the fusion cell line only with cells that specifically produce the monoclonal antibody.

8. The fusion cell line of claim 7, wherein the immunized animal comprises a mouse.

9. The fusion cell line of claim 7, wherein the immortal cell line comprises a myeloma.

10. The fusion cell line of claim 7, wherein the (SEQID No.: 3), (SEQID No.: 4), or (SEQIDNo.:5) is linked to an immunological adjuvant.

11. The fusion cell line of claim 7, wherein the (SEQID No.: 3), (SEQID No.: 4), or (SEQID No.: 5) further comprises a fusion protein.

12. The fusion cell line of claim 11, wherein the fusion protein comprises (SEQID No.: 3), (SEQID No.: 4), or (SEQID No.: 5) fused to a Glutathione S Transferase ("GST") protein.

13. A purified monoclonal antibody that specifically binds to SEQID No.: 3, SEQID No.: 4, or SEQID No.: 5.

14. A fusion cell line that produces a monoclonal antibody that specifically binds to SEQID No.: 3, SEQID No.: 4, or SEQID No.: 5.

* * * * *